US010576350B2

(12) United States Patent
Ishikawa

(10) Patent No.: US 10,576,350 B2
(45) Date of Patent: Mar. 3, 2020

(54) SIMULATION APPARATUS, SIMULATION METHOD, AND SIMULATION SYSTEM

(71) Applicant: Bridgestone Sports Co., Ltd., Tokyo (JP)

(72) Inventor: Tatsuya Ishikawa, Chichibu (JP)

(73) Assignee: Bridgestone Sports Co., Ltd., Tokyo (JP)

(*) Notice: Subject to any disclaimer, the term of this patent is extended or adjusted under 35 U.S.C. 154(b) by 154 days.

(21) Appl. No.: 15/800,230

(22) Filed: Nov. 1, 2017

(65) Prior Publication Data
US 2018/0154236 A1 Jun. 7, 2018

(30) Foreign Application Priority Data

Dec. 2, 2016 (JP) .................. 2016-235250

(51) Int. Cl.
| A63B 71/06 | (2006.01) |
| A63B 69/36 | (2006.01) |
| G09B 19/00 | (2006.01) |
| G16H 20/30 | (2018.01) |
| G06F 17/50 | (2006.01) |
| A63B 60/42 | (2015.01) |

(52) U.S. Cl.
CPC ...... *A63B 69/3608* (2013.01); *A63B 69/3661* (2013.01); *A63B 69/3667* (2013.01); *A63B 69/3676* (2013.01); *A63B 69/3697* (2013.01); *G09B 19/003* (2013.01); *G09B 19/0038* (2013.01); *G16H 20/30* (2018.01); *A63B 60/42* (2015.10); *A63B 2220/806* (2013.01); *G06F 17/5009* (2013.01)

(58) Field of Classification Search
USPC ........................................ 73/65.01
See application file for complete search history.

(56) References Cited

U.S. PATENT DOCUMENTS

| 8,661,879 B2 | 3/2014 | Iwatsubo et al. | |
| 2004/0198524 A1* | 10/2004 | Kwon | A63B 24/0021 473/151 |
| 2007/0196800 A1* | 8/2007 | Douthit | A63B 24/0003 434/252 |
| 2007/0298896 A1* | 12/2007 | Nusbaum | A63B 69/36 473/131 |
| 2013/0157772 A1* | 6/2013 | Ishii | A63B 69/36 473/199 |

(Continued)

FOREIGN PATENT DOCUMENTS

| JP | 2004-242855 A | 9/2004 |
| JP | 2010-011926 A | 1/2010 |

(Continued)

*Primary Examiner* — Andre J Allen
(74) *Attorney, Agent, or Firm* — Sughrue Mion, PLLC

(57) ABSTRACT

A simulation apparatus includes an obtaining unit configured to obtain a measurement result of a test shot of a first golf club performed by a testing golfer, and a calculation unit configured to calculate a simulated ball-striking result which is obtained if the testing golfer strikes a golf ball by a second golf club which has a specification different from the first golf club. The calculation unit determines a swing characteristic of the testing golfer based on the measurement result. The calculation unit calculates the simulated ball-striking result based on the swing characteristic and the measurement result.

9 Claims, 12 Drawing Sheets

(56) References Cited

U.S. PATENT DOCUMENTS

2014/0113262 A1* 4/2014 Kostuj .................. A63B 60/46
434/252
2016/0287966 A1* 10/2016 Fritz .................. A63B 24/0003

FOREIGN PATENT DOCUMENTS

| JP | 2011-115250 A | 6/2011 |
| JP | 2012-239627 A | 12/2012 |
| JP | 2013-031529 A | 2/2013 |
| JP | 2014-023769 A | 2/2014 |

* cited by examiner

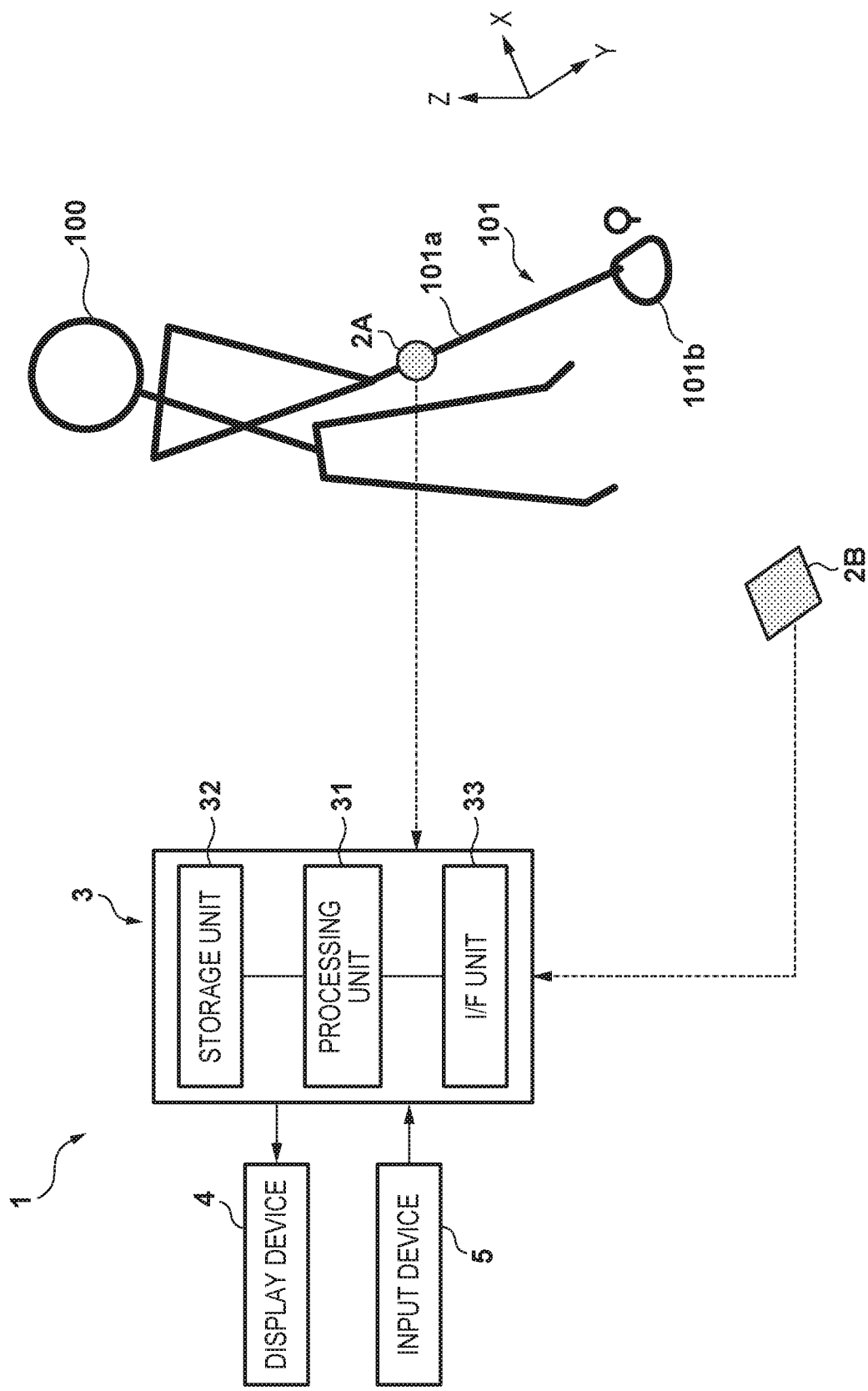

|     | M1  | M2  | M3  | M4  |
|-----|-----|-----|-----|-----|
| #1  | m11 | m21 | m31 | m41 |
| #2  | m12 | m22 | m32 | m42 |
| #3  | m13 | m23 | m33 | m43 |
| #4  | m14 | m24 | m34 | m44 |
| #5  | m15 | m25 | m35 | m45 |
| ⋮   | ⋮   | ⋮   | ⋮   | ⋮   |
| #n  | m1n | m2n | m3n | m4n |

$\theta 7 = \theta 5 - \theta 6$

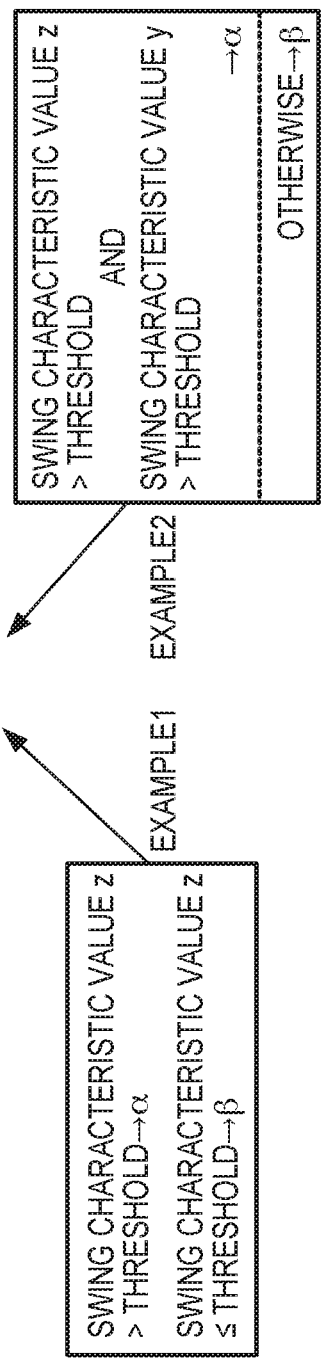

FIG. 10A
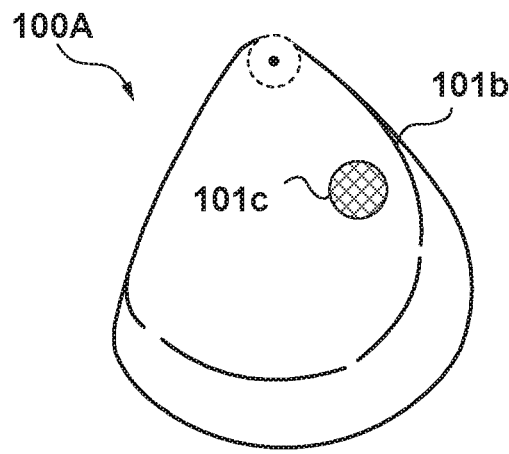
FIG. 10B
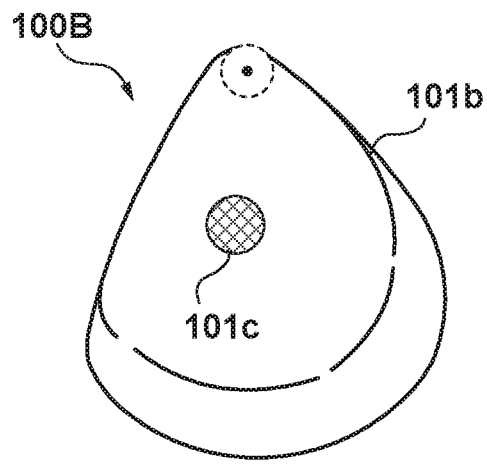
FIG. 10C
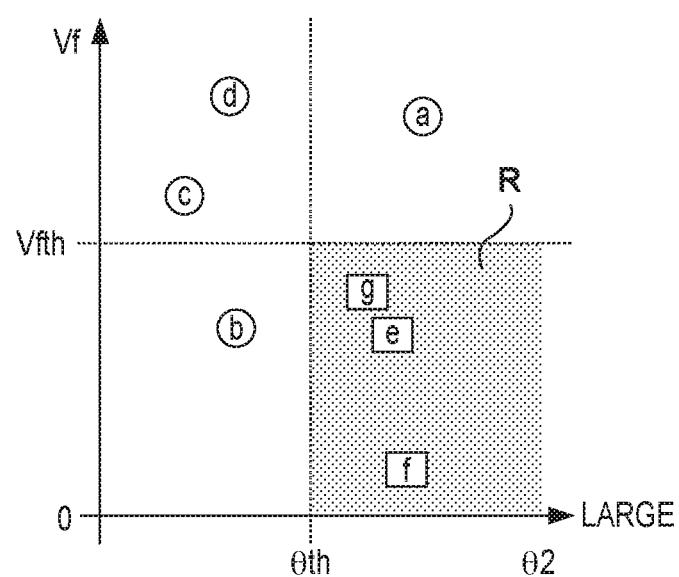
FIG. 10D

SIMULATION APPARATUS, SIMULATION METHOD, AND SIMULATION SYSTEM

BACKGROUND OF THE INVENTION

Field of the Invention

The present invention relates to a golf simulation technique.

Description of the Related Art

In order to facilitate the selection of a golf club which is suitable for an individual golfer, techniques for analyzing a golfer's swing have been proposed (for example, Japanese Patent Laid-Open Nos. 2010-011926, 2014-023769, 2011-115250, 2013-031529, 2004-242855, and 2012-239627).

If a golfer is required to perform test shots with a plurality golf clubs and analyze the test shots in order to select the most suitable golf club for himself/herself, it can place a large burden on the golfer. Hence, it will be convenient for the golfer if a simulated ball-striking result of another golf club can be obtained from a test shot result of one golf club by performing a simulation. However, the convenience of the golfer is reduced if the accuracy of the simulation is low.

SUMMARY OF THE INVENTION

It is an object of the present invention to improve the accuracy of a golf ball striking simulation.

According to one aspect of the present invention, there is provided a simulation apparatus comprising: an obtaining unit configured to obtain a measurement result of a test shot of a first golf club performed by a testing golfer; and a calculation unit configured to calculate a simulated ball-striking result which is obtained if the testing golfer strikes a golf ball by a second golf club which has a specification different from the first golf club, wherein the calculation unit determines a swing characteristic of the testing golfer based on the measurement result, and the calculation unit calculates the simulated ball-striking result based on the swing characteristic and the measurement result.

According to another aspect of the present invention, there is provided a simulation method comprising: obtaining a measurement result of a test shot of a first golf club performed by a testing golfer; and calculating a simulated ball-striking result which is obtained if the testing golfer strikes a golf ball by a second golf club which has a different specification than the first golf club, wherein in the calculating a swing characteristic of the testing golfer is determined based on the measurement result, and the simulated ball-striking result is calculated based on the swing characteristic and the measurement result.

According to still another aspect of the present invention, there is provided a simulation system comprising: a measuring unit configured to measure a test shot of a first golf club performed by a testing golfer; and a calculation unit configured to calculate a simulated ball-striking result which is obtained if the testing golfer strikes a golf ball by a second golf club which has a different specification than the first golf club, wherein the calculation unit determines a swing characteristic of the testing golfer based on a measurement result by the measuring unit, and the calculation unit calculates the simulated ball-striking result based on the swing characteristic and the measurement result.

Further features of the present invention will become apparent from the following description of exemplary embodiments (with reference to the attached drawings).

BRIEF DESCRIPTION OF THE DRAWINGS

FIG. 1 is a schematic view of a simulation system according to one embodiment of the present invention;

FIGS. 8A and 8B are explanatory views of equations;

FIGS. 10A and 10B are explanatory views of a golf club head used for a test;

FIG. 10C is a table showing test results;

FIG. 10D is a graph showing an example of swing characteristic classification;

DESCRIPTION OF THE EMBODIMENTS

First Embodiment

<System Arrangement>

Figures 2A, 2B, 2C:
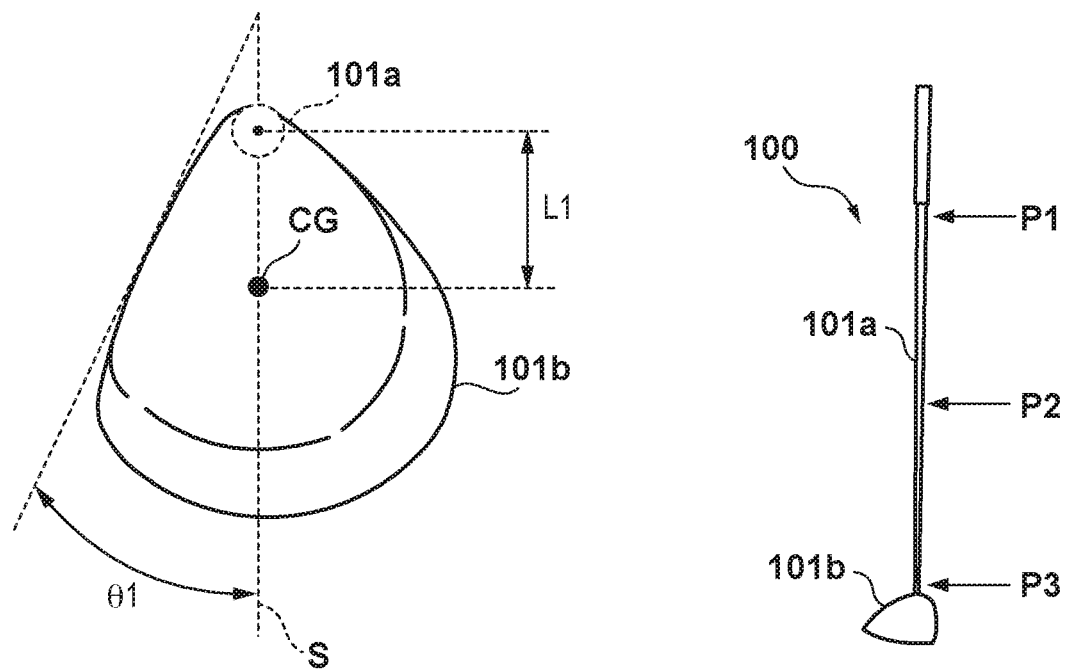
FIG. 2A is an explanatory view of golf club specification information.
FIG. 2B is an explanatory view of a center of gravity angle.
FIG. 2C is an explanatory view of shaft rigidity.

FIG. 1 is a schematic view of a simulation system 1 according to one embodiment of the present invention. The system 1 includes a plurality of measurement devices 2A and 2B, an information processing apparatus 3, a display device 4, and an input device 5. In this embodiment, two types of measurement devices have been provided. However, there may be one type of measurement device or three or more types of measurement devices depending on the measurement contents. Arrows X, Y, and Z indicate the three-dimensional coordinate system of a testing area, the arrows X and Y indicate horizontal directions perpendicular to each other, and the arrow Z indicates the vertical direction. The arrow X is set in the ball line direction of a golf ball.

The measurement device 2A is a device that measures the behavior of a golf club 101 which is used by a testing golfer 100 to make a test shot. In this embodiment, the measurement device 2A is a device which is to be attached to a shaft 101a (or a grip) and includes an acceleration sensor and an angular velocity sensor. For example, TSND 121 of ATR- Promotions, Inc or M-tracer of Seiko Epson Corporation can be used as the measurement device 2A. The movement track of a head 101*b* during a swing, the changes in the face (striking surface), and the impact timing can be measured by the detection result of the measurement device 2A.

The measurement device 2B measures the head speed of the golf club 101 and the ball flight of a shot. In the example of FIG. 1, the measurement device 2B is a ball flight measurement device arranged in the back of the ball line with respect to the golf ball that is to be struck. For example, TRACKMAN of TRACKMAN GOLF can be used as this kind of a measurement device. The initial speed of the shot, the launch angle, the carry of the shot, the back spin amount, the side spin amount, and the like can also be measured by the measurement device 2B.

In this embodiment, the information processing apparatus 3 functions as a simulation apparatus that calculates a simulated ball-striking result and can be formed by a general personal computer. The information processing apparatus 3 includes a processing unit 31, a storage unit 32, and an I/F unit (interface unit) 33 that are electrically connected to each other. The processing unit 31 is a processor such as a CPU. The storage unit 32 includes one or a plurality of storage devices. The storage device is, for example, a RAM, a ROM, a hard disk, or the like. Programs to be executed by the processing unit 31 and various kinds of data are stored in the storage unit 32. A program to be executed by the processing unit 31 can be formed by a plurality of instructions which can be read by the processing unit 31.

The I/F unit 33 performs input and output of data between an external device and the processing unit 31. The I/F unit 33 can include an I/O interface and a communication interface. The measurement devices 2A and 2B are communicably connected to the information processing apparatus 3 by wired or wireless communication, and the respective measurement results are obtained by the information processing apparatus 3.

The display device 4 and the input device 5 are connected to the information processing apparatus 3. The display device 4 is, for example, an electronic image display device such as a liquid crystal display device and displays the processing result of the information processing apparatus 3. The input device 5 is a mouse and a keyboard and accepts data inputs and operation instructions to the information processing apparatus 3.

<Overview of Simulation>

In this embodiment, the information processing apparatus 3 uses the result of a test shot performed by a testing golfer by using a given golf club to calculate a simulated ball-striking result of another golf club which has a different specification. Since the testing golfer can obtain, just by performing a test shot by using a single golf club, information that can serve as a measure when he/she is to use another type of golf club to strike the ball, the testing golfer can more efficiently select a golf club which is suitable for him/her.

In order to execute this kind of simulation, specification information related to specification differences between a plurality of types of golf clubs is stored in the storage unit 32 of the information processing apparatus 3. FIG. 2A is a table showing one example of specification information. In the example of FIG. 2A, pieces of information of specifications M1 to M4 of golf clubs of n types, that is, golf clubs #1 to # n, are included. For example, the specification value of the specification M1 of golf club #1 is represented as m11. In this embodiment, 4 types of specifications M1 to M4 are used. However, 5 or more types of specifications may be used or 3 or fewer types of specifications may be used.

In this embodiment, the specifications M1 to M4 are largely classified into the specifications M1 and M2 which are related to the head 101*b* and the specifications M3 and M4 which are related to the shaft 101*a*. By including the specifications of the head 101*b* and the shaft 101*a*, respectively, each ball-striking result arising from these characteristics can be reflected onto the simulation.

In this embodiment, the specification M1 is the center-of-gravity angle, and the specification M2 is the center-of-gravity distance. FIG. 2B is an explanatory view of the center-of-gravity angle and the center-of-gravity distance. The center-of-gravity angle is the angle made by the vertical direction and the face when a golf club is held to be rotatable about its shaft that is supported horizontally. In FIG. 2B, an angle θ1 made by the face and a vertical broken line S passing through the axis of the shaft 101*a* and a center-of-gravity position CG of the head is the center-of-gravity angle. Note that when the face is a curved surface, a virtual plane in contact with the face center serves as a reference. The center-of-gravity distance is represented by a length L1 from the center-of-gravity position CG of the head to the shaft axis.

In this embodiment, the specification M3 is the rigidity ratio of the proximal end and the distal end of the shaft 101*a*, and the specification M4 is the rigidity of the central portion of the shaft 101*a*. FIG. 2C is an explanatory view of positions on the shaft 101*a*. A position P1 exemplifies the proximal-end position of the shaft 101*a* and is, for example, a position that is 800 mm from the distal end of the shaft. A position P3 exemplifies the distal-end position of the shaft 101*a* and is, for example, a position that is 300 mm from the distal end of the shaft. A position P2 is, for example, a position that is 550 mm from the distal end of the shaft. The value of the specification M3 is, for example, a value obtained by the flexural rigidity value of the position P1/the flexural rigidity value of the position P3. The value of the specification M4 is the flexural rigidity value of the position P2.

Figure 3A:
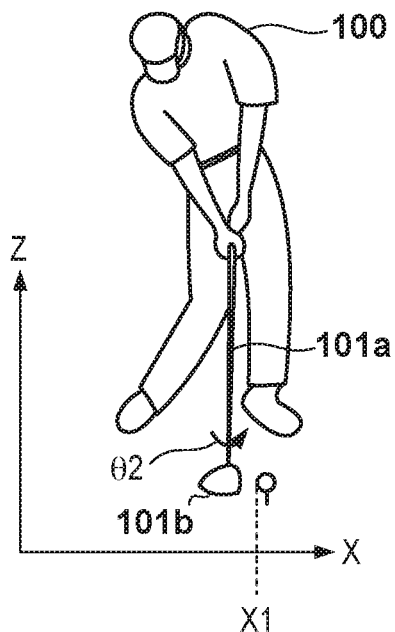
FIG. 3A is an explanatory view of a measurement example of the degree of change of a face.

The main parameters used in a simulation will be described next. FIG. 3A is an explanatory view of the degree of change of the face of the head 101*b*. This degree of change is a parameter related to the face rotation characteristic of the golfer. In this embodiment, a rotation amount θ2 about the axis of the shaft 101*a* per unit time immediately before impact is used as the parameter. The rotation amount θ2 can be measured by the measurement device 2A. The larger the rotation amount θ2, the greater the face rotation in the impact zone is. The unit time is, for example, 0.01 sec immediately before impact. The impact timing can be measured based on the change in the acceleration of the golf club 101, and the position of the head 101*b* at that time may be called an impact position X1.

Figure 3B:
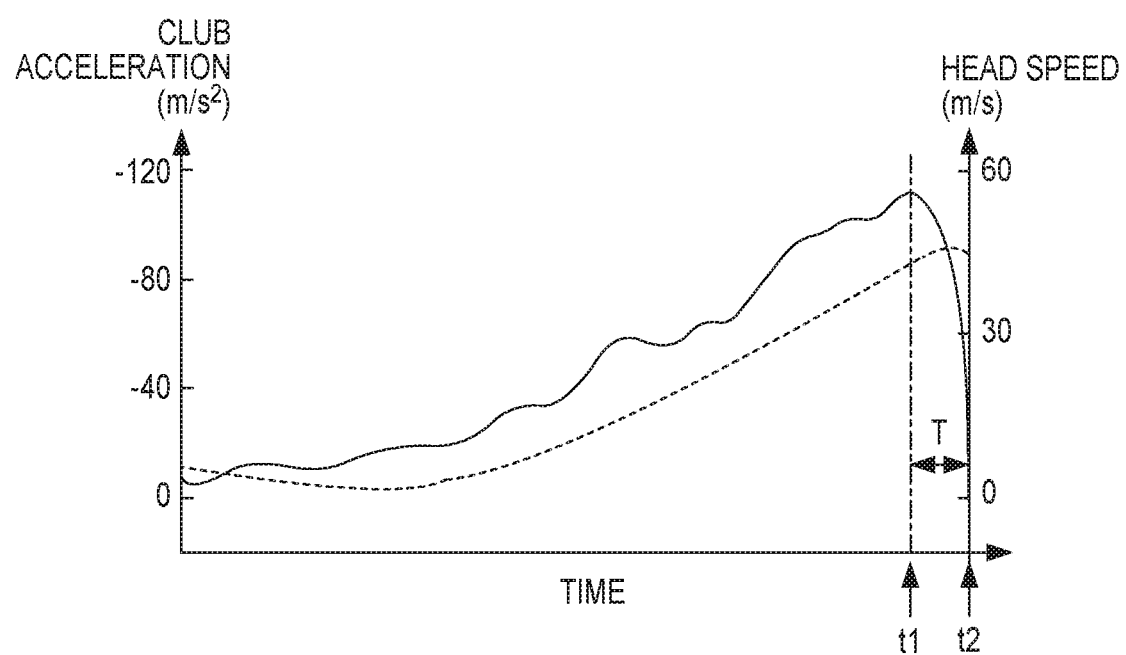
FIG. 3B is an explanatory view of a flexure return time.

FIG. 3B is an explanatory view of a flexure return time. The flexure return time is the duration of time from when a predetermined portion (to be referred to as a measurement portion hereinafter) of a golf club reaches maximum acceleration until impact. This measurement portion may be a position on the shaft adjacent to the distal end of the grip as that in the case of the measurement device 2A in FIG. 1 or another arbitrary position on the golf club may be set as the measurement position. In general, during a golf swing, the shaft 101*a* flexes, from the down swing, in a direction in which the head 101*b* is delayed more than the proximal-end side and tends to achieve impact when the proximal-end side decelerates before impact and the flexure of the 101*a* returns. In other words, the flexure return time is the time taken for the flexure of the shaft 101a to return before impact.

In FIG. 3B, a solid line indicates the temporal acceleration change of a portion of a golf club 101 from the down swing, and a broken line indicates the temporal speed change of the head 101b. A time t1 indicates the timing at which the acceleration of a portion of the golf club 101 has reached the maximum absolute value. The acceleration of the measurement portion of the golf club 101 can be measured by the measurement device 2A. In this case, although the acceleration of a portion on the proximal-end side of the shaft 101a is measured, the acceleration of the head 101b may be measured. A time t2 indicates the impact timing. As already described, the impact timing can be measured, by the measurement device 2A, as the timing at which the acceleration of the golf club 101 has reached the minimum value. The flexure return time is a time T from the time t1 until time t2.

Figure 4A:
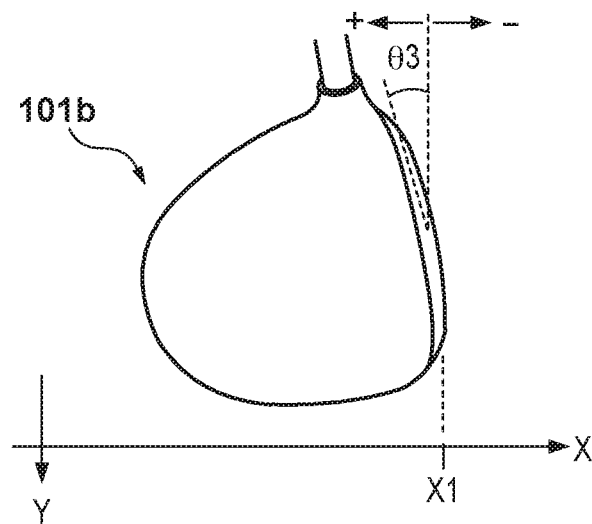
FIG. 4A is an explanatory view of an impact face angle.

FIG. 4A is an explanatory view of an impact face angle. The impact face angle is the direction of the face at impact. In the example of FIG. 4A, an angle θ3 made by the face and the Y direction on an X-Y plane is the impact face angle. According to the measurement by the measurement device 2A, for example, the angle θ3 can be regarded as the reference (0°) at the time of calibration. For example, calibration is processing to cause the measurement device 2A to recognize the target direction. In the example of FIG. 4A, the opening direction of the face is set as the negative angle and the closing direction of the face is set as the positive angle.

Figure 4B:
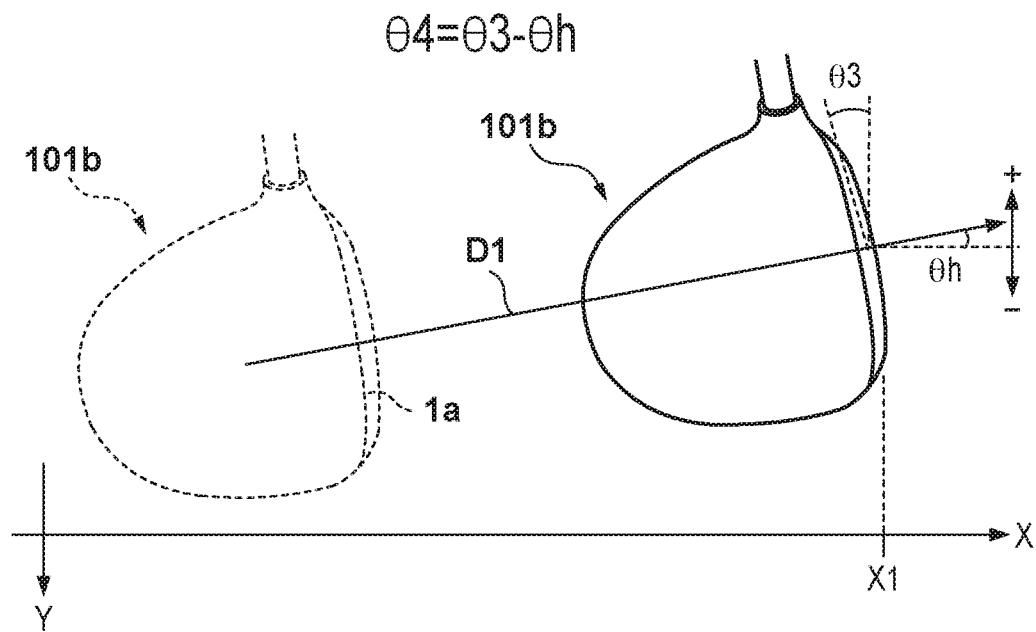
FIG. 4B is an explanatory view of an impact face angle with respect to a head track.

FIG. 4B is an explanatory view of the impact face angle with respect to a head track. The impact face angle with respect to the head track is an angle obtained by correcting the direction of the face at impact by the direction of the head track and is an index of the direction of the face with respect to the head track. In the example of FIG. 4B, a head track direction D1 is specified from the position of the head 101b at a predetermined time before the impact timing and the position of the head 101b at impact, and the angle formed between the D1 direction and the X direction is set as an angle θh. The angle θh is set to have a direction that faces inside with respect to the X direction as the positive angle and to have a direction that faces outside as the negative angle. An impact face angle θ4 with respect to the head track is represented by θ4=θ3−θh.

The angles θ3 and θ4 can be used as indices to determine, as the swing characteristics of the golfer, whether the face has a tendency to become closed (tendency to hook) at impact or has a tendency to become open (tendency to slice) at impact.

Figure 5A:
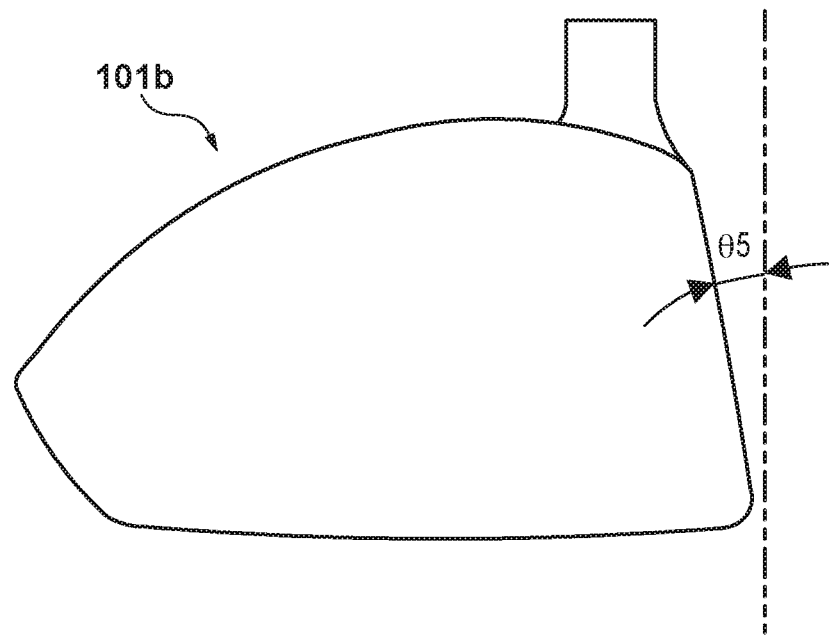
FIG. 5A is an explanatory view of an impact loft angle.

FIG. 5A is an explanatory view of an impact loft angle. The impact loft angle is an angle θ5 made by the face at impact and a vertical surface on the X-Z plane. The angle θ5 can be calculated using the measurement results of the measurement device 2A.

Figure 5B:
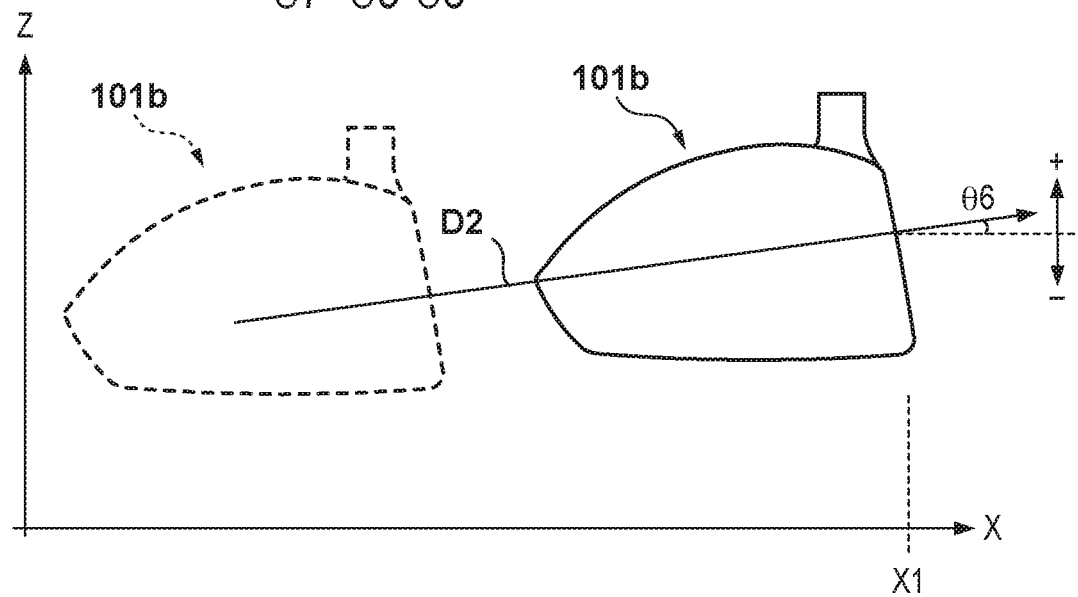
FIG. 5B is an explanatory view of a blow angle.

FIG. 5B is an explanatory view of a blow angle. The blow angle is an angle of the Z-direction track of the head 101b at impact with respect to the X direction on the X-Z plane. In the example of FIG. 5B, the position of a head track direction D2 is specified from the position of the head 101b a predetermined time before the impact timing and the position of the head 101b at impact, and an angle θ6 formed between the D2 direction and the X direction is the blow angle. Assume that the upper direction is set as the positive angle and the lower direction is set as the negative angle. In addition, the difference between the impact loft angle θ5 and the blow angle θ6 is called an impact loft angle with respect to the blow angle, and this angle is represented by θ7 (=θ5−θ6) as shown as in FIG. 5B.

<Example of Simulation Processing>

Figure 6A:
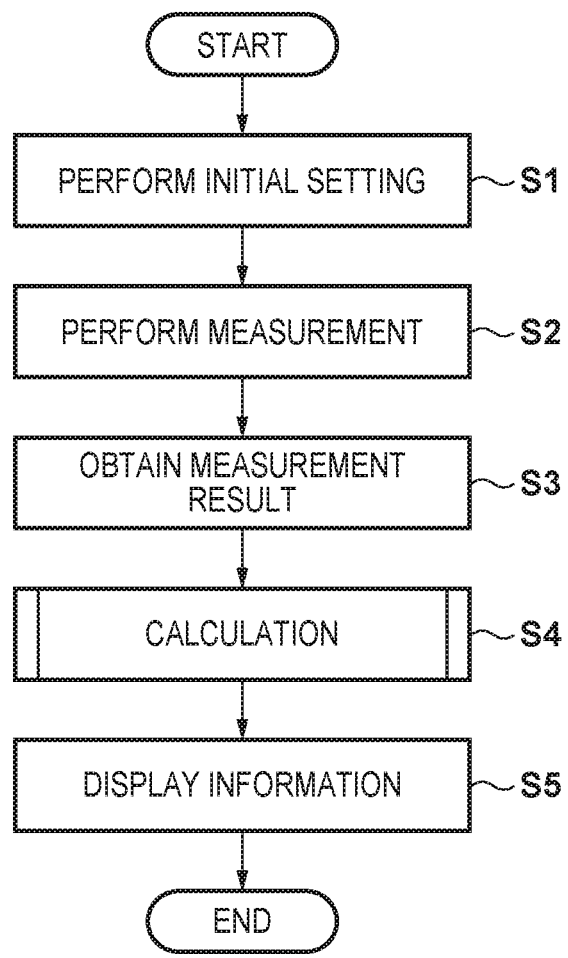
FIGS. 6A and 6B are flowcharts showing an example of processing executed by an information processing apparatus.

An example of the processing program executed by the information processing apparatus 3 will be described with reference to FIG. 6A. FIG. 6A is a flowchart showing an example of the simulation processing which is executed by the processing unit 31. In this embodiment, the testing golfer 100 uses the golf club 101 to make a test shot of a golf ball, and a schematic ball-striking result of a golf club other than that used for the test shot is calculated from the obtained measurement results of the test shot.

In step S1, initial settings are made. Here, the information processing apparatus 3 accepts input of information used to specify the testing club and information of the testing golfer 100.

In step S2, measurement of the test shot is started. Here, the testing golfer 100 is made to actually hit a golf ball by using the golf club 101, and the swing and the shot made by the testing golfer 100 are measured by the measurement devices 2A and 2B.

In step S3, measurement results are obtained from the measurement devices 2A and 2B. In step S4, the information processing apparatus performs a calculation (to be described later) based on each measurement result obtained in step S3. In step S5, information based on the calculation result obtained in step S4 is displayed on the display device 4. Here, for example, the ball-striking result of the testing club and simulated ball-striking results of other types of golf clubs are displayed. The processing of one unit thus ends.

Figure 6B:
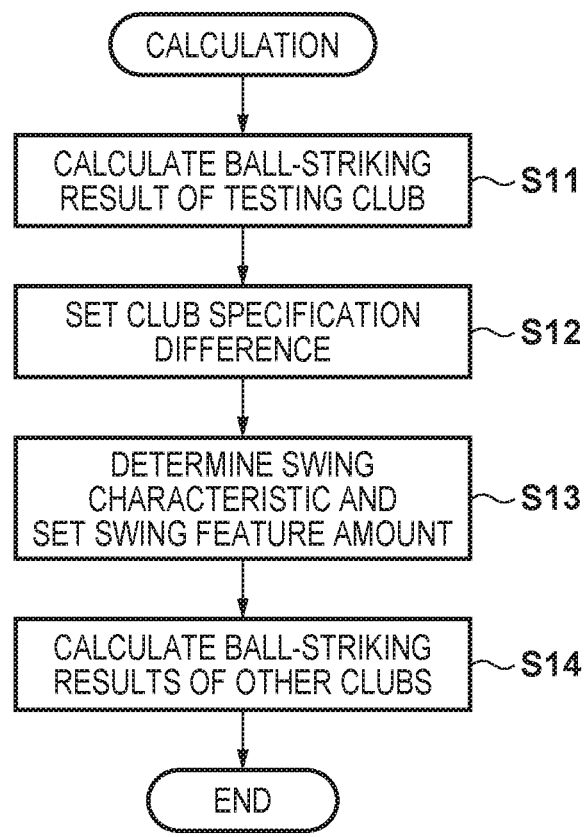

The calculation processing of step S4 will be described with reference FIGS. 6B to 10. FIG. 6B is a flowchart showing an example of the calculation processing in step S4 of FIG. 6B.

Figure 7:
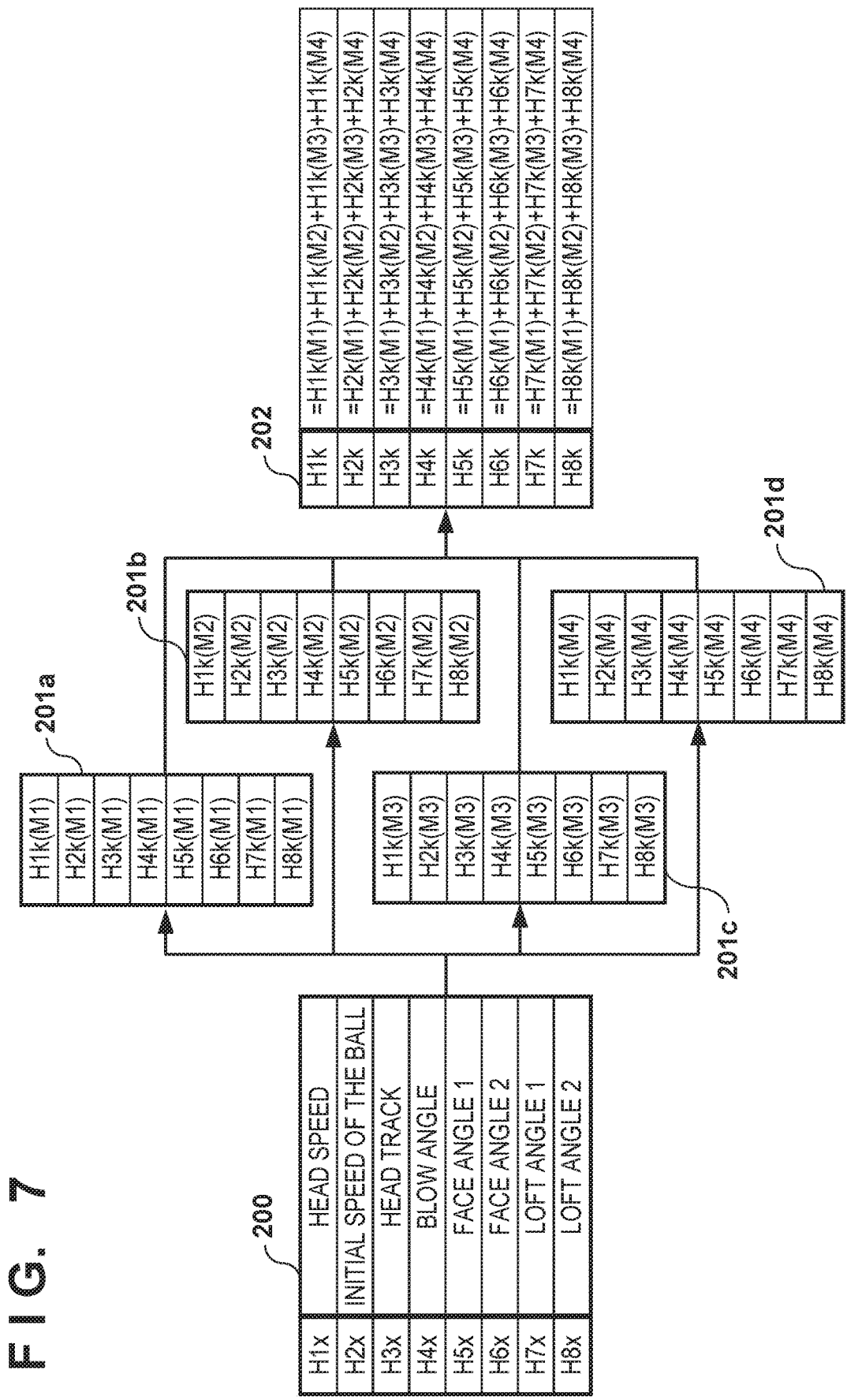
FIG. 7 is a view showing a calculation summary of simulated ball-striking results.

In step S11, the ball-striking results of the testing club are calculated based on the measurement results obtained in step S3. The ball-striking results of the testing club may be measured values, but simulated values derived from the measurement results of the measurement device 2A are used in this embodiment. In this embodiment, 8 types of ball-striking result values H1 to H8, shown in ball-striking results 200 of FIG. 7, are calculated from the angular velocity about the axis of the shaft 101a and the acceleration of the proximal-end side of the golf club 101 that have been measured by the measurement device 2A. A subscript x indicates a value used to discriminate the testing club. The testing club to be discriminated by the subscript x is one golf club among the golf clubs listed on the specification information of FIG. 2A.

The ball-striking result values H1 and H3 to H8 are related to the behavior of the head 101b. These values allow the testing golfer to understand the behavior of the head 101b at impact in his/her swing, and the golfer can use the knowledge to improve his/her swing or club selection. The ball-striking result value H2 is related to the behavior of the shot. The testing golfer can obtain an index of the carry of the shot.

The head speed indicated by the ball-striking result value H1 is the speed of the head 101b at impact. The head speed can be calculated using the measurement result of the measurement device 2A. The initial speed of the ball indicated by the ball-striking result value H2 is the speed of the golf ball immediately after impact. The initial speed of the ball can be calculated by multiplying the ball-striking result value H1 by a coefficient (for example, about 1.4).

The head track indicated by the ball-striking result value H3 is the angle θh shown in FIG. 4B. The blow angle indicated by the ball-striking result value H4 is the angle θ6 shown in FIG. 5B. The head angle and the blow angle can be calculated using the measurement results of the measurement device 2A.

A face angle 1 indicated by the ball-striking result value H5 is the impact face angle θ3 shown in FIG. 4A. The impact face angle θ3 can be calculated using the measurement result of the measurement device 2A. A face angle 2 indicated by the ball-striking result value H6 is the angle θ4 shown in FIG. 4B. The angle θ4 can be calculated from the ball-striking result value H3 and the ball-striking result value H5.

A loft angle 1 indicated by the ball-striking result value H7 is the angle θ5 shown in FIG. 5A. The angle θ5 can be calculated using the measurement result of the measurement device 2A. A loft angle 2 indicated by the ball-striking result value H8 is the angle θ7 shown in FIG. 5B. The angle θ7 can be calculated from the ball-striking result value H7 and the ball-striking result value H4.

Referring back to FIG. 6B, variables necessary for the calculation are set in steps S12 and S13. Club specification differences are set in step S12, and swing characteristics are determined and a swing feature amount is set in step S13. In step S14, the ball-striking results of other golf clubs are calculated, thereby ending the processing of one unit. The contents of steps S12 to S14 will be described hereinafter.

<Calculation Method of Ball-Striking Results of Other Golf Clubs>

An example of the calculation method of simulated ball-striking results of golf clubs other than the testing club will be described with reference to FIG. 7. In this embodiment, ball-striking results 202 of each golf club listed in the table of specification information of FIG. 2A will be calculated from the ball-striking results 200 of the testing club. The ball-striking results 202 are formed from ball-striking result values H1 to H8 in the same manner as the ball-striking result 200 of the testing club. A subscript k indicates a value used to discriminate a calculation target golf club. The ball-striking results 202 are values obtained by adding intermediate values 201a to 201d.

The intermediate values 201a to 201d are simulated values calculated for the specifications M1 to M4, respectively. The intermediate values 201a are simulated values calculated for the ball-striking result values H1 to H8 with respect to the specification M1. The intermediate values 201b are simulated values calculated for the ball-striking result values H1 to H8 with respect to the specification M2. The intermediate values 201c are simulated values calculated for the ball-striking result values H1 to H8 with respect to the specification M3. The intermediate values 201d are simulated values calculated for the ball-striking result values H1 to H8 with respect to the specification M4.

FIG. 8A exemplifies a basic equation for calculating each simulated value of the intermediate values 201a to 201d. The basic equation is a conversion equation for converting the ball-striking result values H1 to H8 of the testing club into ball-striking results for the respective specifications M1 to M4 of another golf club.

The first term on the right-hand side of the basic equation is a test-shot value. The test-shot value indicates a value based on the result of the test shot by the testing club, and one of the ball-striking result values H1x to H8x of FIG. 7 is substituted into the test-shot value.

The second term on the right-hand side of the basic equation is formed by multiplying a value related to the swing feature amount of the testing golfer by a value related to specification difference of a golf club (club specification difference). The value related to the swing feature amount of the testing golfer is calculated by multiplying a characteristic value corresponding to the swing characteristic of the testing golfer by a coefficient 1 (for example, A11) and further adding a coefficient 2 (for example, B11) to the product. The swing characteristics of the testing golfer will be described later.

The club specification differences are differences between the values of the testing club and that of the calculation target golf club with respect to the specifications M1 to M4. For example, assume that the testing club is golf club #1 and the calculation target is golf club #2. In this case, the club specification difference with respect to specification M1 is given by m12−m11, and the club specification difference with respect to the specification M2 is given by m22−m21. In the same manner, the club specification difference with respect to the specification M3 is given by m32−m31, and the club specification difference with respect to the specification M4 is given by m42−m41. The third term on the right-hand side of the basic equation is a coefficient 3 (for example, C11).

As shown in FIG. 8B, the equation of each of simulated values H1k (M1) to H8k (M4) of the intermediate values 201a to 201d is a basic equation of FIG. 8A which has been individually set with the coefficients 1 to 3, and the test shot value, the swing feature amount, and the club specification difference are used as variables. By setting the equation of each of the simulated values H1k (M1) to H8k (M4) to be the same equation by using the basic equation (FIG. 8A), the calculation program can be simplified comparatively. Note that the coefficients 1 to 3 can be obtained by repeating the ball-striking test of a golf club and deriving the coefficients from the measurement results.

<Setting of Swing Characteristics and Variables>

The swing feature amount indicated in the second term on the right-hand side in the basic equation of FIG. 8A will be described next. In the basic equation of FIG. 8A, a ball-striking result difference based on a specification difference between the testing club and the calculation target golf club is simulated by using a parameter called a club specification difference. In general, it is known that the specification of a club and each ball-striking result have a predetermined relationship. For example, a golf club that has a large center-of-gravity angle is considered to have an increased tendency to hook the ball. In other words, the face has a tendency to become closed at impact. Therefore, as a principle, it is preferable for the arrangement of the basic equation to reflect this relationship on the value of each ball-striking result by using each club specification difference value.

However, depending on the testing golfer, this relationship may not be applicable in some cases. Hence, in this embodiment, a swing feature amount term is provided to perform a correction corresponding to the swing characteristic of the testing golfer. That is, in the basic equation of FIG. 8A, it can be said that (coefficient 1*swing feature amount+coefficient 2) represents a correction term corresponding to the swing characteristic.

The relationship between each golf club specification and the swing characteristic can be confirmed by a test. For example, there is a test to check the correlation between each measured value and the simulated value of each ball-striking result between golf clubs that have different specifications. FIGS. 9A to 9D are explanatory views of this concept. Note that the simulated value mentioned here corresponds to a fixed value which does not have the swing feature amount as a variable in the basic equation of FIG. 8A.

Figure 9A:
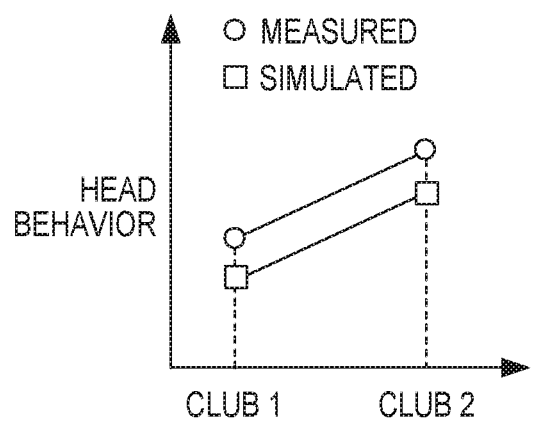
FIGS. 9A to 9D are explanatory views of simulation correction in accordance with a swing characteristic.
Figure 9B:
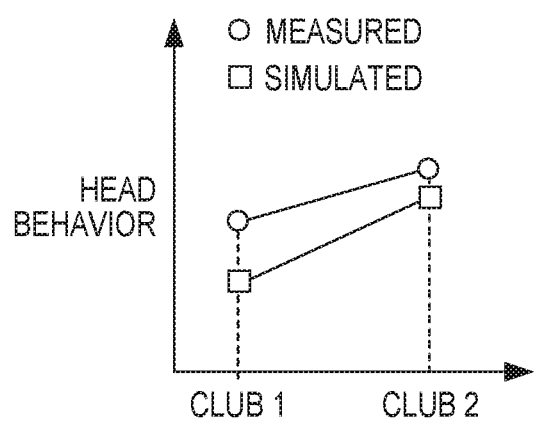

FIG. 9A shows the measured results and the simulated results of head behaviors of golf clubs 1 and 2 in a case in which a golfer A has tested several golf clubs. In the example of FIG. 9A, the simulated results and the measured results are approximately in proportion to each other. FIG. 9B shows, in the same manner, the measured results and the simulated results of the head behaviors of the golf clubs 1 and 2 in a case in which a golfer B, who is different from the golfer A, has tested several golf clubs. The measured results and the simulated results are also approximately in proportion to each other in the case of the example of FIG. 9B.

In the examples of FIGS. 9A and 9B, the simulated results and the measured results are approximately in proportion to each other even when the testing golfer differs. That is, it can be determined that the swing characteristic differences between the golfer A and the golfer B have a small influence on the simulated results.

Figure 9C:
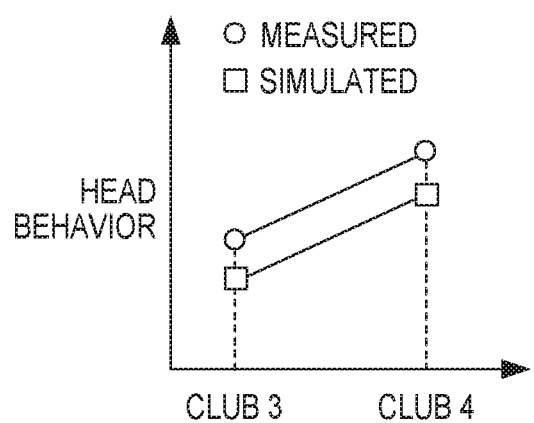
Figure 9D:
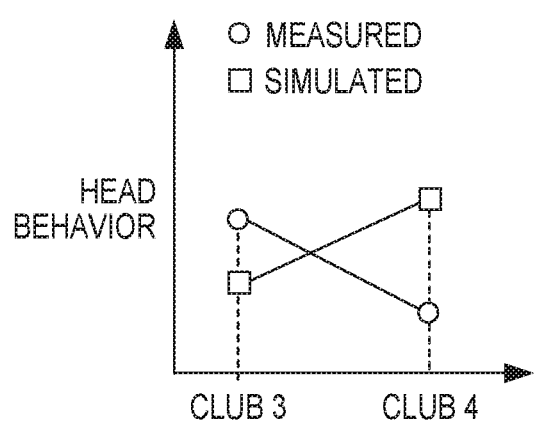

FIG. 9C shows the measured results and the simulated results of head behaviors of golf club 3 and golf club 4 in a case in which the golfer A has tested several golf clubs. In the example of FIG. 9C, the simulated results and the measured results are approximately in proportion to each other. FIG. 9D shows, in the same manner, the measured results and the simulated results of the head behaviors of golf clubs 3 and 4 in a case in which the golfer B has tested several golf clubs. In the example of FIG. 9D, the simulated results and the measured results are in inverse proportion to each other.

In the examples of FIGS. 9C and 9D, the simulated results and the measured results largely differ when the testing golfers differ. That is, it can be determined that the swing characteristic differences between the golfer A and the golfer B have a large influence on the simulated results.

As in the examples of FIGS. 9C and 9D, in a case in which a prominent difference between the simulated results and the measured results appears depending on the testing golfer, it can be considered that there is a correlation, between the specification of the golf club and the swing characteristic of the testing golfer, that needs to be discriminated by the swing characteristics. Although the examples of FIGS. 9A to 9D each exemplified the test results of two golfers, a more universal correlation between the specification of the golf club and the swing characteristic of the testing golfer can be found by performing the same test on a larger number of golfers. Then, the swing feature amount of the second term on the right-hand side in the basic equation of FIG. 8A can be determined from this correlation.

A more specific example of the determination method of the swing feature amount will be described. Here, a test which has found that the correlation between the swing characteristic and the center-of-gravity angle has a different relationship than that of a general idea will be described.

FIGS. 10A and 10B are views for explaining golf clubs 100A and 100B, respectively, which were used for a test. The golf clubs 100A and 100B are golf clubs (drivers, in this case) that have the same specification for portions other than their respective attachment portions of a weight 101c. The weight 101c is attached to the sole portion of each head 101b. The weight 101c is attached relatively to the back side in the golf club 100A, and the weight 101c is attached relatively to the face side in the golf club 100B. The golf club 100A has a larger center-of-gravity angle and has a deeper center-of-gravity depth than the golf club 100B.

In the test, a plurality of testers who have different skill levels each perform test shots a plurality of times by using the golf club 100A and the golf club 100B, and the swing characteristics and the shot characteristics of the testers are measured. As a result, the results shown in FIG. 10C were obtained as the results related to the angles θ3 and θ4. FIG. 10C is a table that has summarized whether the face has a tendency to become closed or open at impact from the differences between the average values of the angles θ3 and θ4 of test shots by the golf club 100A and the average values of the angles θ3 and θ4 of the test shots by the golf club 100B. For example, in a case in which the angle θ3 of the test shot by the golf club 100A is +20° and the angle θ3 of the test shot by the golf club 100B is +15°, since 20−15=+5°, it can be determined that the golf club 100A, which has a large center-of-gravity angle, has an increased tendency to hook. The same applies to the case of the angle θ4. In a case in which the angle θ3 of the test shot by the golf club 100A is +10° and the angle θ3 of the test shot by the golf club 100B is +15°, since 10−15=−5°, it can be determined that the golf club 100A, which has a large center-of-gravity angle, has an increased tendency to slice. The same applies to the case of the angle θ4.

FIG. 10C shows the results of 7 testers a to g. "CL" indicates that the golf club 100A has an increased tendency to hook than the golf club 100B, and "OP" indicates, on the contrary, that the golf club 100A has an increased tendency to slice than the golf club 100B. "-" indicates that there was no significant difference.

The results of FIG. 10C show that the aforementioned general principle related to the center-of-gravity angle applies to the cases of the testers a to d and that a tendency opposite to the general principle related to the center-of-gravity angle applies to the cases of the testers e to g. Hence, by applying the general principle related to the center-of-gravity angle to perform a simulation calculation for a testing golfer who has the same swing characteristic as the testers a to d and by inversely applying the general principle related to the center-of-gravity angle to perform a simulation calculation for a testing golfer who has the same swing characteristic as the testers e to g, it is possible to increase the accuracy of each simulation.

Significant tendencies were observed for a flexure return value Vf and the rotation amount θ2 when the swing characteristics were compared by classifying the testers into the testers a to d and the testers e to g. The flexure return value Vf defined here can be obtained by Flexure return value $Vf=$(maximum acceleration of measured portion of golf club×coefficient $D$)+ (flexure return time $T$×coefficient $E$)+ coefficient $F$ The flexure return value Vf is a value that represents the degree of flexure of the golf club and represents that it is hard to return the flexure at impact as the value is larger. The coefficients D, E, and F can be obtained by repeating the ball-striking test of each golf club and deriving the coefficients from the measurement results.

FIG. 10D is a chart which has set the flexure return value Vf as the ordinate and the rotation amount θ2 as the abscissa and has plotted the corresponding values of the testers a to g. The testers e to g belong to a region R and tend to have comparatively small flexure return values Vf and comparatively large rotation amounts θ2.

Hence, a reference value (threshold) Vfth of the flexure return value Vf and a reference value (threshold) θth of the rotation amount θ2, allowing the discrimination of the testers a to d and the testers e to g, are set as determination conditions for determining the swing characteristics of the testing golfers. The reference value Vfth is, for example, 0.3 and the reference value θth is, for example, 25 rad/sec. Furthermore, the swing characteristics of testing golfers who belong to the region R and those of testing golfers who do not belong to the region R can be classified and set as conditions. Examples 1 and 2 of FIG. 8A respectively show the setting examples (determination condition examples) of the swing feature amount.

Example 1 shows a case in which a value α is substituted as the swing feature amount when one type of swing characteristic value z exceeds the threshold and a case in which a value β is substituted as the swing feature amount when the swing characteristic value z is equal to or less than the threshold. Example 2 shows a case in which the value α is substituted as the swing feature amount when two types of swing characteristic values z and y exceed the corresponding threshold and a case in which value β is substituted in cases other than the preceding case.

The swing feature amount and its determination conditions are defined for each combination of the ball-striking results H1 to H8 and the specifications M1 to M4. Among the combinations of the ball-striking results H1 to H8 and the specifications M1 to M4, there may be a combination that is not influenced by the swing characteristic of the testing golfer. In such a case, a fixed value can be set as the swing feature amount instead of setting a condition in accordance with the swing characteristics of the testing golfers.

The processes of steps S12 to S14 of FIG. 6B will be described further. In step S12, a club specification difference will be calculated from the specification information exemplified in FIG. 2A and set for each of the testing club and the calculation target golf club. In step S14, a swing feature amount is set, from the measurement results obtained in step S3 of FIG. 6A, in accordance with the determination conditions exemplified in examples 1 and 2 of FIG. 8A. In FIG. 7, the intermediate values $201a$ to $201d$ are calculated by substituting the values calculated in steps S11 to S13 in the respective equations of FIG. 8B. The ball-striking results H1$k$ to H8$k$ are calculated by adding the respective calculation results for the ball-striking result values H1 to H8. The ball-striking results H1 to H8 are to be calculated for all of the golf clubs listed in the specification information of FIG. 2A or for each golf club desired by the testing golfer among these golf clubs. The calculated ball-striking results H1 to H8 are to be presented to the testing golfer in step S5 of FIG. 6A.

Second Embodiment

In the first embodiment, the ball-striking results H1$x$ to H8$x$ of the testing club were simulated values derived from the measurement results. In this embodiment, ball-striking results H1$x$ to H8$x$ are calibrated by the shot measurement results obtained by a measurement device 2B, and the ball-striking results H1$x$ to H8$x$ of another golf club are calibrated using the calibration values. As a result, the accuracy of each ball-striking result can be improved.

Figures 11A, 11B, 11C:
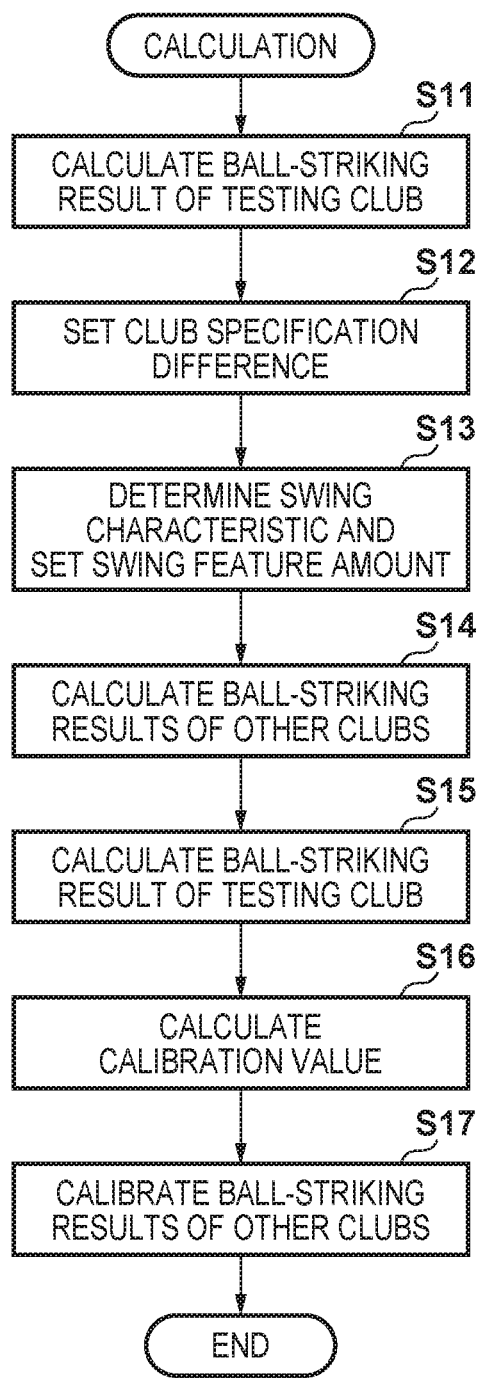
FIG. 11A is a flowchart showing an example of another processing executed by an information processing apparatus.
FIGS. 11B and 11C are explanatory views of simulation result calibration.

FIG. 11A is a flowchart showing an example of the calculation processing of step S4 according to this embodiment. The processes of steps S11 to S14 are the same as those of FIG. 6B in the first embodiment. In step S15, the ball-striking results H1$x$ to H8$x$ of a testing club are calculated based on the shot measurement results (ball flight measurement results) of the measurement device 2B. Here, for example, the initial speed of the ball, the launch angle, the back spin amount, the launch direction, and the side spin amount are used as the shot measurement results. The launch angle is an angle made by the X direction and the shot direction immediately after impact on an X-Z plane. The back spin amount is the shot rotation amount immediately after impact and is the rotation amount about a Y-direction axis. The launch direction is an angle made by the X direction and the shot direction immediately after impact on an X-Y plane. The side spin amount is the shot rotation amount immediately after impact and is the rotation about a Z-direction axis.

The launch angle, the back spin amount, the launch direction, and the side spin amount have the following relations with an impact loft angle θ5, a blow angle θ6, an impact face angle θ3, and a head track θh.

Launch angle=coefficient $a$×impact loft angle−coefficient $b$

Back spin amount=coefficient $c$×(impact loft angle−blow angle)+coefficient $d$

Launch direction=coefficient $e$×impact face angle−coefficient $f$

Side spin amount=coefficient $g$×(impact face angle−head track)+coefficient $h$

The coefficients $\underline{a}$ to h can be obtained by repeating the ball-striking test of a golf club and deriving the coefficients from the measurement results.

In relation with the ball-striking results H1 to H8, the measurement results can be replaced by the following relations.

Launch angle=coefficient $a$×H7−coefficient $b$

Back spin amount=coefficient $c$×(H7−H4)+coefficient $d$

Launch direction=coefficient $e$×H5−coefficient $f$

Side spin amount=coefficient $g$×(H5−H3)+coefficient $h$

From these relations, the values of H3 to H5 and H7 are obtained based on the shot measurement results of the measurement device 2B and the values of H6 and H8 can be further calculated. In addition, the head speed H1 and the initial speed H2 of the ball can be measured by the measurement device 2B. Hence, the ball-striking result values of H1 to H8 can be obtained based on the measurement results of the measurement device 2B and these will be expressed as H1' to H8'.

Calibration values are calculated in step S16. In this embodiment, as exemplified in FIG. 11B, calibration values d1$x$ to d8$x$ related to the testing club are calculated as respective differences between the ball-striking result values H1'$x$ to H8'$x$ based on the measurement results of the measurement device 2B and the ball-striking result values H1$x$ to H8$x$ calculated in step S11 based on the measurement results of the measurement device 2A.

In step S17, the ball-striking results H1$k$ to H8$k$ of a golf club other than the testing club are calibrated by the calibration values calculated in step S16. In this embodiment, as exemplified in FIG. 11C, post-calibration ball-striking results H1'$k$ to H8'$k$ are obtained by adding the calibration values d1$x$ to d8$x$ to the ball-striking results H1$k$ to H8$k$.

Subsequently, the ball-striking result values H1'$x$ to H8'$x$ and H1'$k$ to H8'$k$ are obtained as the final ball-striking results. This can improve the accuracy of each simulation.

Third Embodiment

In the first embodiment, the measurement results of the measurement device 2A were used when the ball-striking results H1x to H8x of the testing club were calculated in step S11 of FIG. 6B. However, as described in the second embodiment, the ball-striking results H1x to H8x of the testing club can be calculated from the measurement results of the measurement device 2B. Hence, the ball-striking results H1x to H8x of the testing club in step S11 of FIG. 6B can be calculated from the measurement results of the measurement device 2B. The processes of steps S12 to S14 of FIG. 6B are the same as those in the first embodiment. Thus, it is possible to obtain ball-striking result values having the same accuracy as the post-calibration ball-striking results $H1'x$ to $H8'x$ and $H1'k$ to $H8'k$ of the second embodiment.

Other Embodiments

The system of FIG. 1 exemplified a system that can be installed in a shop or the like by arranging measurement devices 2A and 2B and an information processing apparatus 3 in a comparatively close distance from each other. However, another arrangement example is adoptable. Also, a device other than that of FIG. 1 is adoptable as each measurement device.

Figure 12:
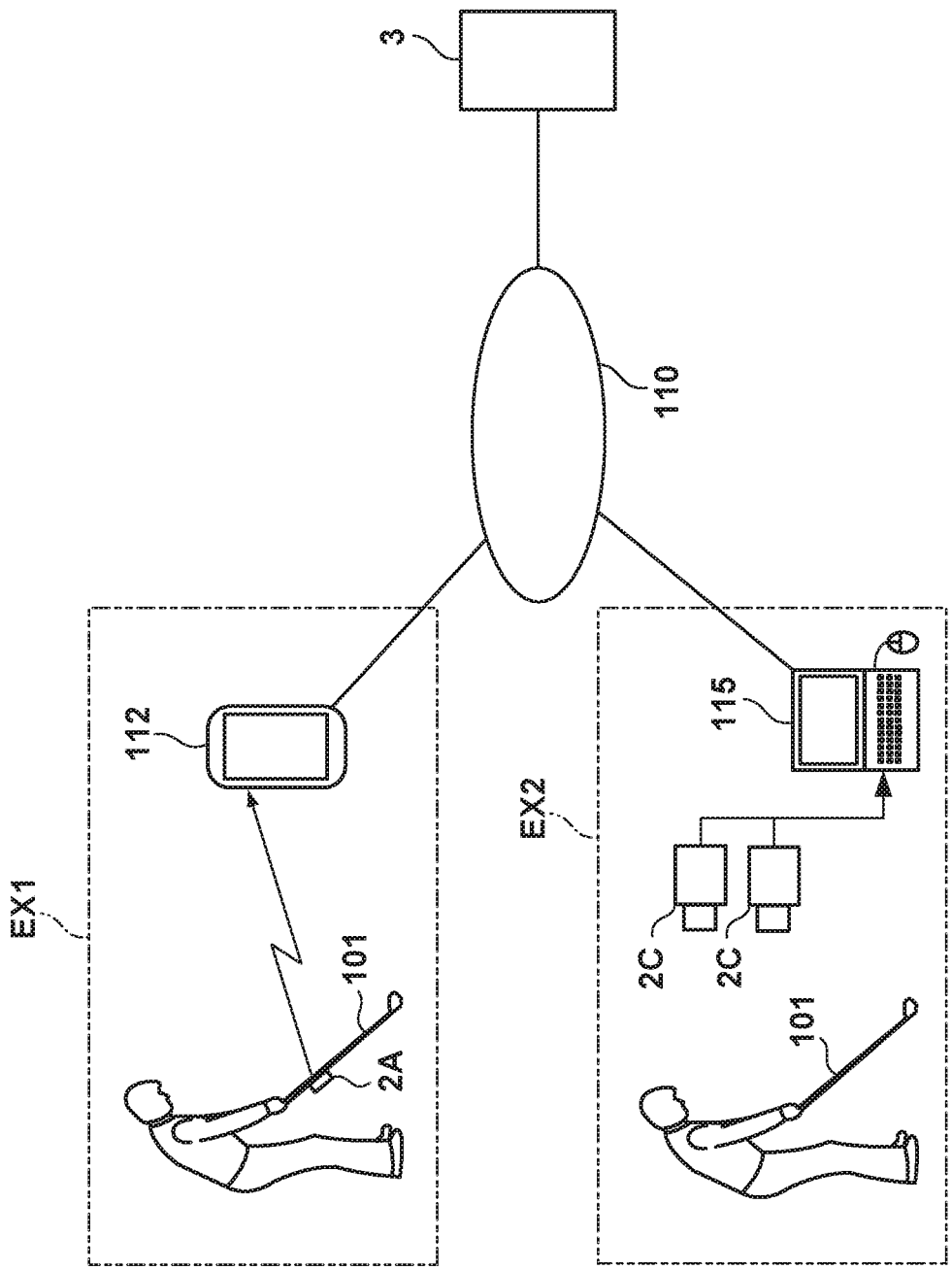
FIG. 12 is a view showing another example of a simulation system.

FIG. 12 shows another arrangement example of a simulation system 1. In the arrangement example of FIG. 12, the information processing apparatus 3 can serve as a server to communicate with a communication device (such as a portable terminal 112 or a personal computer 115) via a network 110 and distribute information related to each golf club. The network 110 is, for example, the Internet.

A measurement-side arrangement example Ex1 includes the portable terminal 112 and the measurement device 2A and is a system suited for a golfer to personally measure his/her swing characteristics. The portable terminal 112 is, for example, a smartphone and includes a short-range wireless communication function with the measurement device 2A and a wireless communication function via the network 110 and a base station (not shown). The measurement results of the measurement device 2A are transmitted to the portable terminal 112. The portable terminal 112 transmits, to the information processing apparatus 3, the received measurement results as is or as data of a predetermined format which is processable on the side of the information processing apparatus 3. The information processing apparatus 3 calculates the ball-striking result values and transmits the obtained information to the portable terminal 112. The portable terminal 112 displays the received information. That is, the processes of steps S1, S2, and S5 of FIG. 6A are executed in the portable terminal 112, and the processes of steps S3 and S4 are executed in the information processing apparatus 3.

A measurement-side arrangement example Ex2 includes the personal computer 115 and a plurality of measurement devices 2C and is a system suited for measuring the swing characteristics of a golfer in a golf shop or the like. Each measurement device 2C is an image capturing apparatus such as a video camera. The personal computer 115 includes a function to process the images captured by the image capturing devices 2C and a wireless communication function via the network 110. The golfer performs the test shot in a test shot room or the like. The three-dimensional behavior of a golf club 101 and the behavior of the shot are captured by capturing the testing golfer from various directions by the plurality of image capturing apparatuses 2C in the test shot room. The captured images are loaded and analyzed in the personal computer 115 and subsequently transmitted to the information processing apparatus 3 as data of a predetermined format which is processable on the side of the information processing apparatus 3. The information processing apparatus 3 calculates the ball-striking result values and transmits the information to the personal computer 115. The personal computer 115 displays the received information. That is, the processes of steps S1, S2, and S5 of FIG. 6A are executed in the personal computer 115, and the processes of steps S3 and S4 are executed in the information processing apparatus 3.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefits of Japanese Patent Application No. 2016-235250, filed Dec. 2, 2016, which is hereby incorporated by reference herein in its entirety.

What is claimed is:

1. A simulation apparatus comprising:
at least one processor configured to implement:
an obtaining unit configured to obtain a measurement result of a test shot of a first golf club performed by a testing golfer; and
a calculation unit configured to calculate a simulated ball-striking result which is obtained if the testing golfer strikes a golf ball by a second golf club which has a specification different from the first golf club,
wherein the calculation unit determines a swing characteristic of the testing golfer based on the measurement result, and
the calculation unit calculates the simulated ball-striking result based on the swing characteristic and the measurement result.

2. The apparatus according to claim 1, wherein the calculation unit calculates the simulated ball-striking result by changing a variable, which is to be substituted in a calculation equation for calculating the simulated ball-striking result, in accordance with the swing characteristic.

3. The apparatus according to claim 1, further comprising:
a storage unit configured to store information related to a specification difference among the plurality of types of golf clubs,
wherein the calculation unit calculates the simulated ball-striking result based on the swing characteristic, the measurement result, and the information.

4. The apparatus according to claim 3, wherein the information includes a plurality of types of characteristics related to a head and a plurality of types of characteristics related to a shaft.

5. The apparatus according to claim 1, wherein the simulated ball-striking result includes at least a plurality of types of results related to a behavior of a head of the second golf club at impact.

6. The apparatus according to claim 5, wherein the plurality of types of results include at least a head speed, a head track, a blow angle, a face direction, and/or a loft angle.

7. The apparatus according to claim 1, wherein the swing characteristic at least includes
a characteristic related to a degree of change of a face, and
a characteristic related to the maximum acceleration of a predetermined portion of a golf club and a time from when the predetermined portion reaches the maximum acceleration until impact.

8. A simulation method comprising:
obtaining a measurement result of a test shot of a first golf club performed by a testing golfer; and calculating a simulated ball-striking result which is obtained if the testing golfer strikes a golf ball by a second golf club which has a different specification than the first golf club,
wherein in the calculating
a swing characteristic of the testing golfer is determined based on the measurement result, and
the simulated ball-striking result is calculated based on the swing characteristic and the measurement result.

9. A simulation system comprising:
a measuring device configured to measure a test shot of a first golf club performed by a testing golfer; and
at least one processor configured to implement:
an obtaining unit configured to obtain a measurement result of the test shot of the first golf club based on the test shot measured by the measurement device; and
a calculation unit configured to calculate a simulated ball-striking result which is obtained if the testing golfer strikes a golf ball by a second golf club which has a different specification than the first golf club,
wherein the calculation unit determines a swing characteristic of the testing golfer based on a measurement result by the measuring unit, and
the calculation unit calculates the simulated ball-striking result based on the swing characteristic and the measurement result.

* * * * *